(12) United States Patent
Wo et al.

(10) Patent No.: US 6,362,265 B1
(45) Date of Patent: Mar. 26, 2002

(54) ADDITIVES WITH REDUCED RESIDUAL TIN CONTENT AND THERMOPLASTIC COMPOSITIONS CONTAINING THE SAME

(75) Inventors: Shiming Wo, Dacula, GA (US); Ji Li, Ste-Foy-les-Lyon (FR)

(73) Assignee: Rhodia INC, Cranbury, NJ (US)

( * ) Notice: Subject to any disclaimer, the term of this patent is extended or adjusted under 35 U.S.C. 154(b) by 0 days.

(21) Appl. No.: 09/449,892

(22) Filed: Nov. 30, 1999

Related U.S. Application Data

(60) Provisional application No. 60/110,870, filed on Dec. 4, 1998, now abandoned.

(51) Int. Cl.[7] .................. C08K 5/101; C08K 5/103
(52) U.S. Cl. .............. 524/315; 554/161; 560/129; 560/179; 560/205
(58) Field of Search ............. 554/161; 560/129, 560/179, 205; 524/315

(56) References Cited

U.S. PATENT DOCUMENTS

| | | | |
|---|---|---|---|
| 4,205,023 A | | 5/1980 | Anzerberger |
| 4,264,534 A | | 4/1981 | Anzenberger |
| 4,487,874 A | * | 12/1984 | Lindner ............ 524/311 |
| 4,960,866 A | | 10/1990 | Bendix et al. |
| 5,011,629 A | * | 4/1991 | Bilbo ............... 524/306 |
| 5,238,985 A | | 8/1993 | O'Lenick, Jr. |
| 5,286,397 A | * | 2/1994 | Schmid ............. 524/314 |
| 5,606,103 A | | 2/1997 | Trapasso et al. |

FOREIGN PATENT DOCUMENTS

| | | |
|---|---|---|
| EP | 0 288 320 | 10/1988 |
| EP | 0 933 352 A | 8/1999 |
| WO | 8903853 | * 5/1989 |

* cited by examiner

*Primary Examiner*—Margaret Medley
*Assistant Examiner*—Cephia D. Toomer
(74) *Attorney, Agent, or Firm*—Watov & Kipnes, P.C.

(57) ABSTRACT

Additives obtained from the catalytically induced esterification reaction of a mono- or polyhydroxy alkanol and at least one carboxylic acid employing a complexing agent selected from dicarboxylic acids or anhydrides thereof to substantially reduce the residual tin content and thermoplastic compositions and articles produced thereby.

45 Claims, No Drawings

ADDITIVES WITH REDUCED RESIDUAL TIN CONTENT AND THERMOPLASTIC COMPOSITIONS CONTAINING THE SAME

RELATED APPLICATION

The present application relies for priority purposes on provisional patent application U.S. Ser. No. 60/110,870 filed on Dec. 4, 1998, now abandoned.

FIELD OF THE INVENTION

The present invention is generally directed to a process for the catalytically induced esterification of a mono- or polyhydroxy alkanol with at least one carboxylic acid in which the residual tin catalyst content is significantly reduced. At least one dicarboxylic acid or anhydride thereof is employed as an agent for removing residual tin to provide an additive having little or no hazing for use in making a thermoplastic composition.

BACKGROUND OF THE INVENTION

Esters of mono- or polyhydroxy alkanols are produced by reacting the alkanol with at least one carboxylic acid in the presence of a tin containing catalyst. The resulting additive may be used as a mold releasing agent in the production of a variety of useful polymeric compounds including, but not limited to, polycarbonates.

Thermoplastic compositions, containing the present additives, produced in this manner may be placed in a mold to form a molded article. It is often desirable for some thermoplastic compositions to add a mold-releasing agent which facilitates the removal of the molded article from the mold. The mold releasing agent is typically combined with the thermoplastic composition, mixed thoroughly, and then the resulting mixture is formed into solid components such as chips which are then remelted and placed in the mold.

It is known that the presence of residual tin in the additives may produce a haze which detracts from the appearance of the final product. The hazing occurs over time at room temperature and is caused by the slow precipitation of tin, typically in the form of a tin-containing salt (e.g. stannous carboxylates). The haze material eventually settles to the bottom of the container and becomes a second phase. If the residual tin is not removed from the additive, the thermoplastic plastic composition may be adversely affected.

Efforts have been made to remove the residual tin from the additive through the employment of various complexing agents including mono-acids and salts thereof, such as disclosed in Anzenberger, Sr., U.S. Pat. No. 4,264,534, European Patent Publication No. 0288320, and Bendix et al., U.S. Pat. No. 4,960,866. An aqueous alkaline composition having a pH greater than about 13.2 has been used for the same purpose as disclosed in Trapasso et al., U.S. Pat. No. 5,606,103. Such processes have been disadvantageous because the amount of tin that is removed by the addition of the complexing agent is insufficient to substantially eliminate haze and/or such processes employ organic solvents which add to the cost of the process and also raises environmental concerns. A further disadvantage of some prior art process is that they treat the ester at a relatively high pH which makes the ester prone to hydrolysis. Some prior art processes add water to the esters which can create an emulsion which makes separation of the esters more difficult.

It would therefore be a significant advance in the art of producing additives for the production of polymeric compounds and especially polycarbonates through the esterification of a mono- or polyhydroxy alkanol and at least one carboxylic acid, if the presence of haze-forming residual tin in the additive can be eliminated or substantially reduced.

It would be a further advance in the art if the removal of residual tin can be accomplished without the use of organic solvents.

SUMMARY OF THE INVENTION

The present invention is generally directed to a process of producing an additive by the esterification of a mono- or polyhydroxy alkanol with at least one carboxylic acid in the presence of a tin containing catalyst with at least the substantial elimination of residual tin. To this end a complexing agent in the form of at least one dicarboxylic acid or anhydride thereof is employed. The complexing agent forms an easily removable precipitate with the residual tin. The esterification reaction and subsequent removal of residual tin is accomplished without the use of organic solvents and without the addition of water so that an emulsion is not formed. The process of the present invention can reduce the residual tin content to below about 300 ppm, preferably less than about 15 ppm, and most preferably no more than about 3 ppm. In accordance with the present invention, the residual tin content is significantly reduced by the employment of a complexing agent selected from dicarboxylic acids and anhydrides thereof.

In a particular aspect of the present invention, there is provided a process for the catalytically induced esterification of a mono- or polyhydroxy alkanol with at least one carboxylic acid in the presence of a tin-containing catalyst with a reduced residual tin content comprising:

a) reacting the mono- or polyhydroxy alkanol and the at least one carboxylic acid in the presence of a tin-containing catalyst to produce a liquid medium containing said ester and up to a residual amount of tin;

b) adding to said liquid medium an effective amount of a complexing agent selected from the group consisting of dicarboxylic acids and anhydrides thereof to thereby precipitate an amount of the residual tin from the liquid medium sufficient to substantially eliminate hazing of the liquid medium;

c) removing the precipitated residual tin from the liquid medium.

Additives for use in thermoplastic compositions produced in accordance with the present process and thermoplastic compositions are also encompassed by the present application.

DETAILED DESCRIPTION OF THE INVENTION

In accordance with the present invention, there is provided a process for the catalytically induced esterification of a mono- or polyhydroxy alkanol and at least one carboxylic acid having a reduced residual tin content. The residual tin from the catalyst is then removed from the liquid reaction medium through the employment of a complexing agent selected from the group consisting of dicarboxylic acids and anhydrides thereof. The preferred complexing agents are those of the formula:

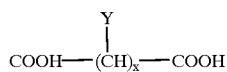

wherein x is selected from 0 to 6 and Y is selected from the group consisting of hydrogen and a substituted or unsubstituted branched or straight chain alkyl group or alkenyl group, preferably having from 1 to 8 carbon atoms. The substituents may be preferably selected from alkyl groups preferably having from 1 to 4 carbon atoms. Anhydrides of the above-mentioned dicarboxylic acids may also be employed in the present invention. The preferred dicarboxylic acids are adipic acid, succinic acid, maleic acid and oxalic acid.

Anhydrides of the above-mentioned acids may also be employed in the present invention. Preferred anhydrides are those based on succinic acid and include N- or iso-alkyl and alkenyl succinic anhydrides. Specific examples include, but are not limited to, N- and iso-butenyl succinic anhydrides, N- and iso-butyl succinic anhydrides, and the like.

The amount of the complexing agent is based, in part, on the amount of residual tin in the reaction medium. The amount of the complexing agent can range from less than to greater than a stoichmetric amount. By way of example, a stoichiometric amount of the complexing agent adipic acid may be calculated in the following manner.

Amount of Adipic Acid=amount of tin-containing catalyst×% of tin in the tin-containing catalyst (e.g. 27% for stannous octanoate)×1.232 (molecular weight of adipic acid÷molecular weight of tin).

The complexing agent can be used in any catalytically induced esterification process for the reaction of a mono- or polyhydroxy alkanol with at least one carboxylic acid. Typical examples of the carboxylic acids are those having from 8 to 22 carbon atoms such as stearic acid, 12-hydroxy stearic acid and lauric acid. The preferred alcohols are those having from 3 to 36 carbon atoms with C-20 guerbet alcohol being a preferred alcohol for use in the present invention.

The preferred tin-containing catalysts are those that are at least substantially soluble in the reaction mixture and which react to form an insoluble precipitate with the complexing agent employed in the present invention. Preferred tin-containing catalysts include stannous octanoate, stannous oxalate, and hydrated monobutyltin oxide. The preferred tin-containing catalyst is stannous octanoate.

The temperature of the esterification reaction may vary depending on the reactants (acid and alkanol) selected. In accordance with the present invention, the temperature of the precipitation reaction (i.e. when the complexing agent is added to the reaction medium) is desirably at a temperature sufficient to effectively enable the residual tin and complexing agent to form a precipitate. It will be understood that the selected temperature for solid complexing agents may be above or below the melting point of the complexing agent. Typical precipitation reaction temperatures are in the range of from about 100 to 180° C. For example, the precipitation reaction using adipic acid as the complexing agent may be effectively conducted at a precipitation reaction temperature of about 130° C. By adding a desirable amount of the complexing agent to the reaction medium it is possible to achieve tin levels below about 300 ppm, preferably below about 15 ppm, and down to as low as 3 ppm or less. When tin is removed in this manner, hazing of the final additive product is at least significantly reduced if not eliminated.

The precipitate formed by the complexing agent and the residual tin may be removed in any convenient manner, preferably by filtering which may be typically conducted at about room temperature up to the temperature employed in the precipitation reaction, preferably from about 80 to 100° C.

The removal of residual tin is conducted in the absence of organic solvents such as acetone, dimethylacetamide, dioxane, tetrahydrofuran, dimethylformamide and the like commonly employed in esterification processes. The elimination or organic solvents makes the present processes for the formation of additives for thermoplastic compositions more environmentally desirable.

EXAMPLE 1

Isoarachedyl alcohol (hydroxyl number=182) was charged into a 1 L flask equipped with a distillation apparatus. The moisture content of the alcohol was checked to ensure that it was less than 0.1%. 300 g of 12-hydroxy stearic acid (acid number=182) was charged into the flask followed by 0.96 g of stannous octanoate (stannous tin %=27%). The batch was heated to 220° C. and held until the acid number was below 5 mg KOH/g. After three hours the acid number was found to be 1.0 mg KOH/g. During the holding period, about 16 to 20 g of distillate was collected.

The batch was then cooled to 120° C. and then 210 g of stearic acid (acid number=207) and 1.85 g of stannous octanoate were added. The reaction mixture was heated to 220° C. under a vacuum of 40 mmHg for 30 minutes. Thereafter the vacuum was released and the batch maintained at 220° C. for 4 hours.

Thereafter a vacuum of 20 to 30 mm was applied and held until the acid number and the hydroxyl number were below 5 and 10 mg KOH/g, respectively. In this particular example, the acid number was 4 mg KOH/g and the hydroxyl number was 6 mg KOH/g. Thereafter the vacuum was released.

The batch was cooled to 125–130° C. and once the temperature was reached, 0.94 g of powdered adipic acid was added. The batch turned cloudy and was stirred for 2 hours and then cooled to 80° C. The batch was filtered through a 10 micron filter paper and then refiltered with 1 micron paper. The finished product was clear at room temperature and contained less than 3 ppm of tin.

EXAMPLE 2

An ester formulation was prepared in accordance with Example 1. The batch was thereafter cooled to 125–130° C. and 0.70 g of powdered adipic acid was added. The batch was stirred for 2 hours and then cooled to 80° C. The batch was filtered in the same manner as described in Example 1.

The finished product was clear at room temperature and contained less than 15 ppm of tin.

EXAMPLE 3

An ester formulation was prepared in accordance with Example 1 except that the batch was cooled to 155° C. and then 0.76 g of succinic acid was added and stirred for 2 hours. The batch was cooled to 80° C. and was filtered in the same manner as Example 1.

The finished product was clear at room temperature and contained less than 15 ppm of tin.

What is claimed is:

1. A process for the catalytically induced esterification of a mono- or polyhydroxy alkanol and at least one carboxylic acid with a reduced residual tin content comprising:

a) reacting the mono- or polyhydroxy alkanol and at least one carboxylic acid in the presence of a tin-containing catalyst to produce a liquid medium containing said ester with up to a residual amount of tin;

b) adding to said liquid medium an effective amount of a complexing agent selected from the group consisting of dicarboxylic acids and anhydrides thereof to thereby precipitate an amount of said residual tin from the liquid medium sufficient to substantially eliminate hazing of the liquid medium; and c) removing the precipitated tin from the liquid medium.

2. The process of claim 1 wherein the complexing agent has the formula:

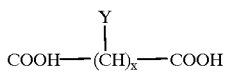

wherein x is selected from 0 to 6 and Y is selected from the group consisting of hydrogen, and a substituted or unsubstituted branched or straight chain alkyl group or alkenyl group having from 1 to 8 carbon atoms.

3. The process of claim 2 wherein the substituents are selected from alkyl groups having from 1 to 4 carbon atoms.

4. The process of claim 1 wherein the complexing agent is selected from the group consisting of adipic acid, succinic acid, oxalic acid, maleic acid and anhydrides thereof.

5. The process of claim 4 wherein the anydrides are selected from the group consisting of N- and iso-butenyl succinic anhydrides and N- and iso-butyl succinic anhydrides.

6. The process of claim 1 wherein the alkanol has from 3 to 36 carbon atoms.

7. The process of claim 6 wherein the alkanol is a C-20 guerbet alcohol.

8. The process of claim 1 wherein the at least one carboxylic acid has from 8 to 22 carbon atoms.

9. The process of claim 8 wherein the at least one carboxylic acid is selected from the group consisting of stearic acid, 12-hydroxy stearic acid and lauric acid.

10. The process of claim 1 wherein the tin-containing catalyst is selected from the group consisting of stannous octanoate, stannous oxalate and hydrated monobutyltin oxide.

11. The process of claim 1 wherein the esterification reaction is conducted at a temperature of from about 150 to 300° C.

12. The process of claim 1 comprising conducting step (b) at a precipitation temperature at which the complexing agent forms a precipitate with the residual tin.

13. The process of claim 1 wherein step (c) is conducted at a temperature of from about room temperature up to the precipitation temperature employed in step (b).

14. A thermoplastic composition comprising:
a) a thermoplastic material;
b) an additive obtained from the catalytically induced esterification of a mono- or polyhydroxy alkanol and at least one carboxylic acid with a reduced residual tin content, said process comprising:
1) reacting the mono- or polyhydroxy alkanol and at least one carboxylic acid in the presence of a tin-containing catalyst to produce a liquid medium containing said ester with up to a residual amount of tin;
2) adding to said liquid medium an effective amount of a complexing agent selected from the group consisting of dicarboxylic acids and anhydrides thereof to thereby precipitate an amount of said residual tin from the liquid medium sufficient to substantially eliminate hazing of the liquid medium; and
3) removing the precipitated tin from the liquid medium.

15. The thermoplastic composition of claim 14 having no more than about 300 ppm of residual tin.

16. The thermoplastic composition of claim 14 having no more than about 15 ppm of residual tin.

17. The thermoplastic composition of claim 14 wherein the complexing agent has the formula:

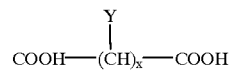

wherein x is selected from 0 to 6 and Y is selected from the group consisting of hydrogen, and a substituted or unsubstituted branched or straight chain alkyl group or alkenyl group having from 1 to 8 carbon atoms.

18. The thermoplastic composition of claim 17 wherein the substituents are selected from alkyl groups having from 1 to 4 carbon atoms.

19. The thermoplastic composition of claim 14 wherein the complexing agent is selected from the group consisting of adipic acid, succinic acid, oxalic acid, maleic acid and anhydrides thereof.

20. The thermoplastic composition of claim 19 wherein the anhydrides are selected from the group consisting of N- and iso-butenyl anhydrides and N- and iso-butyl succinic anhydrides.

21. The thermoplastic composition of claim 14 wherein the alkanol has from 3 to 36 carbon atoms.

22. The thermoplastic composition of claim 21 wherein the alkanol is a C-20 guerbet alcohol.

23. The thermoplastic composition of claim 14 wherein the at least one carboxylic acid has from 8 to 22 carbon atoms.

24. The thermoplastic composition of claim 23 wherein the at least one carboxylic acid is selected from the group consisting of stearic acid, 12-hydroxy stearic acid and lauric acid.

25. The thermoplastic composition of claim 14 wherein the tin-containing catalyst is selected from the group consisting of stannous octanoate, stannous oxalate and hydrated monobutyltin oxide.

26. The thermoplastic composition of claim 14 wherein the esterification reaction is conducted at a temperature of from about 150° to 300° C.

27. The thermoplastic composition of claim 14 comprising conducting step (2) at a precipitation temperature at which the complexing agent forms a precipitate with the residual tin.

28. The additive of claim 14 wherein step (c) is conducted at a temperature of from about room temperature up to about the precipitation temperature employed in step (b).

29. The thermoplastic composition of claim 14 wherein the thermoplastic material is a polycarbonate.

30. The thermoplastic plastic composition of claim 14 in the form of a molded article.

31. A process for the preparation of a thermoplastic composition comprising adding an additive to a thermoplastic material said additive produced by a process comprising:
a) reacting a mono- or polyhydroxy alkanol and at least one carboxylic acid in the presence of a tin-containing catalyst to produce a liquid medium containing said ester with up to a residual amount of tin;
b) adding to said liquid medium an effective amount of a complexing agent selected from the group consisting of dicarboxylic acids and anhydrides thereof to thereby precipitate an amount of said residual tin from the liquid medium sufficient to substantially eliminate hazing of the liquid medium; and c) removing the precipitated tin from the liquid medium.

32. The process of claim 31 wherein the complexing agent has the formula:

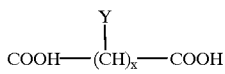

wherein x is selected from 0 to 6 and Y is selected from the group consisting of hydrogen, and a substituted or unsubstituted branched or straight chain alkyl group or alkenyl group having from 1 to 8 carbon atoms.

33. The process of claim 32 wherein the substituents are selected from alkyl groups having 1 to 4 carbon atoms.

34. The process of claim 32 wherein the additive has no more than about 300 ppm of residual tin.

35. The additive of claim 32 wherein the additive has no more than about 15 ppm of residual tin.

36. The process of claim 32 wherein the complexing agent is selected from the group consisting of adipic acid, succinic acid, oxalic acid, maleic acid and anhydrides thereof.

37. The process of claim 36 wherein the anhydrides are selected from the group consisting of N- and iso-butenyl succinic anhydrides and N- and iso-butyl succinic anhydrides.

38. The process of claim 32 wherein the alkanol has 3 to 36 carbon atoms.

39. The process of claim 38 wherein the alkenol is a C-20 guerbet alcohol.

40. The process of claim 32 wherein the at least one carboxylic acid has from 8 to 22 carbon atoms.

41. The process of claim 32 wherein the at least one carboxylic acid is selected from the group consisting of stearic acid, 12-hydroxy stearic acid and lauric acid.

42. The process of claim 32 wherein the tin-containing catalyst is selected from the group consisting of stannous octanoate, stannous oxalate and hydrated monobutylin oxide.

43. The process of claim 32 wherein the esterification reaction is conducted at a temperature of from about 150 to 300° C.

44. The process of claim 32 comprising conducting step (b) at a precipitation temperature at which the complexing agent forms a precipitate with the residual tin.

45. The process of claim 32 wherein step (c) is conducted at a temperature of from about room temperature up to about the precipitation temperature employed in step (b).

* * * * *